United States Patent
Chen et al.

(10) Patent No.: US 10,520,495 B2
(45) Date of Patent: Dec. 31, 2019

(54) DISSOLUTION-ENHANCED TIME-RESOLVED FLUOROIMMUNOASSAY BASED ON RARE EARTH NANOMATERIAL

(71) Applicant: FUJIAN INSTITUTE OF RESEARCH ON THE STRUCTURE OF MATTER, CHINESE ACADEMIC OF SCIENCES, Fuzhou, Fujian (CN)

(72) Inventors: Xueyuan Chen, Fujian (CN); Shanyong Zhou, Fujian (CN); Wei Zheng, Fujian (CN); En Ma, Fujian (CN); Mingdong Huang, Fujian (CN); Zhuo Chen, Fujian (CN); Datao Tu, Fujian (CN)

(73) Assignee: FUJIAN INSTITUTE OF RESEARCH ON THE STRUCTURE OF MATTER, CHINESE ACADEMIC OF SCIENCES, Fuzhou, Fujian (CN)

( * ) Notice: Subject to any disclaimer, the term of this patent is extended or adjusted under 35 U.S.C. 154(b) by 0 days.

(21) Appl. No.: 15/128,803

(22) PCT Filed: Aug. 22, 2014

(86) PCT No.: PCT/CN2014/085075
§ 371 (c)(1),
(2) Date: Sep. 23, 2016

(87) PCT Pub. No.: WO2015/143830
PCT Pub. Date: Oct. 1, 2015

(65) Prior Publication Data
US 2017/0108491 A1   Apr. 20, 2017

(30) Foreign Application Priority Data
Mar. 27, 2014  (CN) .......................... 2014 1 0118864

(51) Int. Cl.
*G01N 33/542* (2006.01)
*G01N 33/533* (2006.01)
*G01N 33/58* (2006.01)

(52) U.S. Cl.
CPC ......... *G01N 33/542* (2013.01); *G01N 33/533* (2013.01); *G01N 33/587* (2013.01); *G01N 33/588* (2013.01); *G01N 2458/40* (2013.01)

(58) Field of Classification Search
CPC .. G01N 33/588; G01N 33/533; G01N 33/587; G01N 33/542; G01N 2458/40
See application file for complete search history.

(56) References Cited

U.S. PATENT DOCUMENTS

| 4,565,790 A * | 1/1986 | Hemmila | G01N 33/539 436/537 |
| 7,381,567 B2 * | 6/2008 | Hemmila | C12Q 1/682 435/6.13 |

FOREIGN PATENT DOCUMENTS

| CN | 102236020 A | 11/2011 |
| CN | 102305854 A | 1/2012 |

(Continued)

OTHER PUBLICATIONS

Nichkova, M. et al., "Microarray Immunoassay for Phenoxybenzoic Acid Using Polymer Encapsulated Eu:Gd2O3 Nanoparticles as Fluorescent Labels", Analytical Chemistry, vol. 77, No. 21, Nov. 1, 2005, pp. 6864-6873, ISSN: 0003-2700.

*Primary Examiner* — Shafiqul Haq
(74) *Attorney, Agent, or Firm* — Novick, Kim & Lee, PLLC; Allen Xue

(57) ABSTRACT

This invention relates to a rare earth nanomaterial labeled biomolecule, its labeling method and a dissolution-enhanced time-resolved fluoroimmunoassay based on the rare earth nanomaterial. The rare earth nanomaterial serves as a label having stable properties, large specific surface area, strong (Continued)

modifiability, low-cost and thousands of lanthanide ions contained in each nanocrystal, the labeling ratio of rare earth ions can be greatly improved. Furthermore, the rare earth nanomaterial can be less affected by exogenous rare earth ions, unaffected by anticoagulants, and has broader applicability; after the immune complex was formed by labeling the biomolecules with the nanomaterial containing rare earth, an enhancer solution was added to allow the rare earth nanomaterial to dissolve into the rare earth ions, which can in turn form new signaling molecules with the chelates in the enhancer solution to induce intramolecular and intermolecular energy transfer, thereby significantly increasing fluorescence intensity by about a million times to greatly enhance the detection sensitivity by using time-resolved fluorescence assay.

8 Claims, 5 Drawing Sheets

(56) References Cited

FOREIGN PATENT DOCUMENTS

| CN | 102604637 A | 7/2012 |
|---|---|---|
| CN | 103224787 A | 7/2013 |
| CN | 103969432 A | 8/2014 |

\* cited by examiner

DISSOLUTION-ENHANCED TIME-RESOLVED FLUOROIMMUNOASSAY BASED ON RARE EARTH NANOMATERIAL

TECHNICAL FIELD

The present invention relates to a rare earth nanomaterial used for labeling biomolecules, the labeling method using the nanomaterial and the fluoroimmunoassay mediated by the nanomaterial, specifically relates to a rare earth nanomaterial for labeling biomolecules, the labeling method using the nanomaterial and a dissolution-enhanced time-resolved fluoroimmunoassay based on the rare earth nanomaterial.

BACKGROUND ART

The technique of radioimmunoassay (RIA) because of the disadvantages, such as radioactive contamination, short half-lives, short shelf-life, and so on, will be abandoned. The sensitivity and reproducibility of enzyme-linked immunosorbent assay (ELISA) are not better than those of radioimmunoassay, and the enzymatic activity and stability of chromogenic substrates remain to be improved. Chemiluminescence immunoassay (CLIA) because of short-lived light emission and unrepeatable detection, susceptibility to environmental interference and expensive reagents, cannot be widely used.

By contrast, time-resolved immunoassay (TRFIA) with high sensitivity, low background, good stability and wide linear ranges now has been widely recognized as the most promising nonradioactive labeled immunoassay. In recent years, the analysis systems have been developed described as follows:

Dissociation-enhanced lanthanide time-resolved fluoroimmunoassay (DELFIA): the most widely used, consists of a tracer, a bifunctional chelating agent and an enhancer. Fluorescence enhancement is one of the important factors to achieve extremely high sensitivity. Lanthanide ions forming microcapsules with an enhancer solution can effectively prevent luminescence-quenching by water molecules, thus greatly enhancing the fluorescence intensity of the system. In addition, the bifunctional chelating agent is also one of the key factors, and a labeling ratio between europium ion as the first selected label and protein is between 10 and 20. But the bifunctional chelating agent as the label issusceptible to interference caused by external substances such as exogenous rare earth ions, ethylenediaminetetraacetic acid, heparin and other anticoagulants. The test sample must be serum, which has very strict operational requirements and is rather expensive.

Solid-phase time-resolved fluoroimmunoassay (FIAgen) is a time-resolved immunoassay using bifunctional rare earth chelating agents as labels. It has an advantage that fluorescence can be directly detected without the need for adding an enhancer solution, but its sensitivity of the detection is much lower than DELFIA.

Moreover, fluorescent nanoparticles coated with rare earth chelates are also used in time-resolved immunoassay. Each nanoparticle contains thousands of rare earth chelates. Therefore, the detection sensitivity is greatly improved, but it is affected by instability of rare earth chelates, such as easy leaking, susceptibility to photobleaching, and so on.

It should be mentioned that rare earth nanomaterials have advantages such as stable property, large specific surface area, strong modifiability, low synthetic cost, and so on, and have recently been generally recognized as a promising and new generation of fluorescent labels for biological materials. However, the luminescence of rare earth nanomaterials is via absorption of light and sensitized luminescence through the intra-4f configuration transitions within the rare earth ions, which gives a low molar extinction coefficient and leads to weak luminescence. Hence, when rare earth nanomaterials are used as labels for direct detection, their applications are limited by the low sensitivity.

CONTENTS OF THE INVENTION

The present invention aims to overcome the deficiencies of the above prior art to provide a highly sensitive biomolecule labeling method with a rare earth nanomaterial which can be used in time-resolved fluoroimmunoassay. Another object of the present invention is to provide a dissolution-enhanced time-resolved fluoroimmunoassay based on a rare earth nanomaterial.

The present invention hereby provides the following technical solutions:

A rare earth nanomaterial labeled biomolecule used in time-resolved fluoroimmunoassay, wherein said biomolecule includes biotin, avidin, antibody or aptamer; and said rare earth nanomaterial contains one or more selected from europium, samarium, terbium, dysprosium.

According to the present invention, said biomolecule is labeled via chemical coordination method or physical adsorption method.

According to the present invention, said rare earth nanomaterial is selected from nanocrystals of rare earth fluorides, rare earth oxides, rare earth fluorine oxides, rare earth chlorine oxides, rare earth phosphates, rare earth borates, rare earth silicates, rare earth molybdates, rare earth tungstates, rare earth carbonate which containing one or more selected from europium, samarium, terbium, dysprosium.

According to the present invention, said rare earth nanomaterial is preferably $XYF_4$ nanocrystals, wherein said X is one or more selected from lithium, sodium, potassium, etc., and said Y is one or more selected from europium, samarium, terbium, dysprosium.

The present invention also provides the following technical solutions:

A labeling method for labeling biomolecule with the rare earth nanomaterial used in time-resolved fluoroimmunoassay, wherein said rare earth nanomaterial labels biomolecule via chemical coordination method or physical adsorption method, said biomolecule including biotin, avidin, antibody or aptamer.

According to the present invention, said rare earth nanomaterial contains one or more selected from europium, samarium, terbium, dysprosium.

According to the present invention, said rare earth nanomaterial is one or more selected from nanocrystals of rare earth fluorides, rare earth oxides, rare earth fluorine oxides, rare earth chlorine oxides, rare earth phosphates, rare earth borates, rare earth silicates, rare earth molybdates, rare earth tungstates, rare earth carbonate which containing europium, samarium, terbium, dysprosium.

According to the present invention, said rare earth nanomaterial is preferably $XYF_4$ nanocrystal, said X is one or more selected from lithium, sodium, potassium, etc., and said Y is one or more selected from europium, samarium, terbium, dysprosium.

The present invention also provides the following technical solutions:

A dissolution-enhanced time-resolved fluoroimmunoassay method based on rare earth nanomaterial, wherein said method utilizes the above-mentioned rare earth nanomaterial labeled biomolecules used in time-resolved fluoroimmunoassay.

According to the present invention, said method comprises: adding the above-mentioned rare earth nanomaterial labeled biomolecules used in time-resolved fluoroimmunoassay to form the immune complex, and then adding an enhancer solution to allow the rare earth nanomaterial to dissolve and exist in the form of rare earth ions, thereby forming molecules having strong fluorescence signals (rare earth nanomicelles) with chelates in the enhancer solution to detect fluorescence signals using time-resolved assay.

According to the present invention, said method comprises the following steps of:

1) immobilizing a capture antibody or antigen on a microplate through physical adsorption or covalent coupling;
2) blocking the plate with a blocking solution;
3) adding a sample containing the detection antigen or antibody to be detected;
4) adding the above-mentioned rare earth nanomaterial labeled biomolecules used in time-resolved fluoroimmunoassay to form an immune complex;
5) adding an enhancer solution and detecting fluorescence signals using the time-resolved assay.

According to the present invention, upon addition of the detection antigen to be detected, said biomolecule is selected from biotin, avidin, antibody or aptamer.

According to the present invention, upon addition of the detection antibody to be detected, said biomolecule is selected from biotin, avidin or aptamer.

According to the present invention, said step 4) can be:
adding the above-mentioned rare earth nanomaterial labeled antibody used in time-resolved fluoroimmunoassay to form an immune complex;

According to the present invention, said step 4) can also be separated into the following steps:
(a) adding a biotin-labeled antibody;
(b) adding the above-mentioned rare earth nanomaterial labeled avidin used in time-resolved fluoroimmunoassay to form an immune complex;

According to the present invention, said step 4) can also be separated into the following steps:
(a') adding a biotin-labeled antibody;
(b') adding avidin;
(c') adding the above-mentioned rare earth nanomaterial labeled biotin used in time-resolved fluoroimmunoassay to form an immune complex;

According to the present invention, said rare earth nanomaterial contains one or more selected from europium, samarium, terbium, dysprosium.

According to the present invention, said rare earth nanomaterial is selected from nanocrystals of rare earth fluorides, rare earth oxides, rare earth fluorine oxides, rare earth chlorine oxides, rare earth phosphates, rare earth borates, rare earth silicates, rare earth molybdates, rare earth tungstates, rare earth carbonate which containing one or more selected from europium, samarium, terbium, dysprosium.

According to the present invention, said rare earth nanomaterial is preferably $XYF_4$ nanocrystals, wherein said X is one or more selected from lithium, sodium, potassium, etc. and said Y is one or more selected from four elements of europium, samarium, terbium, dysprosium.

According to the present invention, said labeling method of the rare earth nanomaterial labeling biotin, avidin, antibody or aptamer is chemical coordination method or physical adsorption method.

According to the present invention, said blocking solution is the conventional solution in the present field, which is commercially available or can be synthesized. Said blocking solution can be bovine serum albumin (BSA) blocking solution or ethanolamine blocking solution.

According to the present invention, said enhancer solution can be a conventional enhancer solution in the field, and preferably said enhancer solution mainly consists of a buffer solution, β-diketone, a nonionic surfactant and a synergistic agent.

According to the present invention, said buffer solution is selected from Triton X-100, said β-diketone is selected from naphthoyltrifluoroacetone, said nonionic surfactant is selected from tri-n-octylphosphine oxide, and said synergistic agent is selected from water.

According to the present invention, said enhancer solution mainly consists of Triton X-100, naphthoyltrifluoroacetone, tri-n-octylphosphine oxide, and distilled water.

According to the present invention, the detection mode includes sandwich assay, direct assay or competitive assay.

In the present invention, said $XYF_4$ nanocrystals such as $NaEuF_4$ nanocrystals can be prepared by a method known to those skilled in the art. For example, said nanocrystals can be prepared via the following method:

1) weighing out $Eu(Ac)_3$, adding it into the mixed solvent of oleic acid and octadecylene, stirring to dissolve at 160° C. under nitrogen atmosphere to obtain a solution A;
2) weighing out $NH_4F$ and NaOH, adding them into methanol to dissolve to give a solution B;
3) after the solution A was cooled down to room temperature, slowly adding the solution B dropwise into the solution A with a dropper, excluding air, increasing temperature to 60° C. under nitrogen atmosphere, and stirring to remove methanol;
4) increasing temperature to 120° C., and stirring the reaction to remove residual water;
5) increasing temperature to 300° C. and stirring the reaction;
6) after the solution was cooled down to room temperature, adding anhydrous ethanol to precipitate nanocrystals;
7) optionally, centrifuging, washing with anhydrous ethanol; preferably, washing three times. Other methods for preparing $XYF_4$ nanocrystals can refer to the above-described method.

According to the present invention, said biomolecules can be labeled via chemical coordination method. Said chemical coordination method is known to those skilled in the art. Taking the biotin labeled by NaEuF4 nanocrystals via chemical coordination method as an example, the process can be described as follows:

1) weighing out oil-soluble $NaEuF_4$ nanocrystals to dissolve in hydrogen chloride-ethanol solution, ultrasonicating, collecting the nanoparticles by centrifugation, washing with anhydrous ethanol to remove oleic acid on the surface of the nanocrystals, and adding deionized water to dissolve to obtain water-soluble nanocrystals;
2) taking the water-soluble nanocrystals synthesized in step 1), adding biotin and ammonia water, ultrasonicating, centrifuging and washing with deionized water, and finally dissolving in deionized water.

According to the present invention, said biomolecules can be labeled via physical adsorption method. Said physical adsorption method is known to those skilled in the art. Taking the biotin labeled by $NaEuF_4$ nanocrystals via physical adsorption method as an example, the process can be described as follows:

1) weighing out oil-soluble NaEuF$_4$ nanocrystals to dissolve in hydrogen chloride-ethanol solution, ultrasonicating, collecting the nanoparticles by centrifugation, washing with anhydrous ethanol to remove oleic acid on the surface of the nanocrystals, and adding deionized water to dissolve to obtain water-soluble nanocrystals;

2) taking the water-soluble nanocrystals synthesized in step 1), adding an antibody, adding a phosphate buffer solution, shaking at room temperature, collecting the nanoparticles by centrifugation, washing with water, and dissolving in the buffer solution.

The present invention has the following beneficial effects:

1) The rare earth nanomaterial was used for biomolecule labeling. Because the rare earth nanomaterial has stable properties, large specific surface area, strong modifiability, low-cost and thousands of lanthanide ions contained in each nanocrystal particle, the labeling ratio of rare earth ions can be greatly improved. Furthermore, the rare earth nanomaterial can be less affected by exogenous rare earth ions, unaffected by anticoagulants, and has broader applicability.

2) after the biomolecules labeled with the nanomaterial containing rare earth formed the immune complex, an enhancer solution was added to allow the rare earth nanomaterial to dissolve into the rare earth ions, which can in turn form new signaling molecules with the chelates in the enhancer solution to induce intramolecular and intermolecular energy transfer, thereby significantly increasing fluorescence intensity by about a million times to greatly enhance the detection sensitivity. Specifically, the detection sensitivity of the present invention is 900 times higher than that of the commercial time-resolved carcinoembryonic antigen assay kits.

3) as shown in the comparison in FIG. 1, by the method of the present invention, due to thousands of rare earth ions being contained in each rare earth nanocrystal particle, the labeling ratio of rare earth ions has been greatly improved so that fluorescence signals and detection sensitivity have been significantly enhanced.

Wherein, it is shown that the antigen or antibody to be detected is labeled by (a) the rare earth chelate or (b) the rare earth nanomaterial with double antibody sandwich method, and after the formation of immune complex, the enhancer solution is added and the fluorescence signals are detected by using the time-resolved method.

Figure 1:
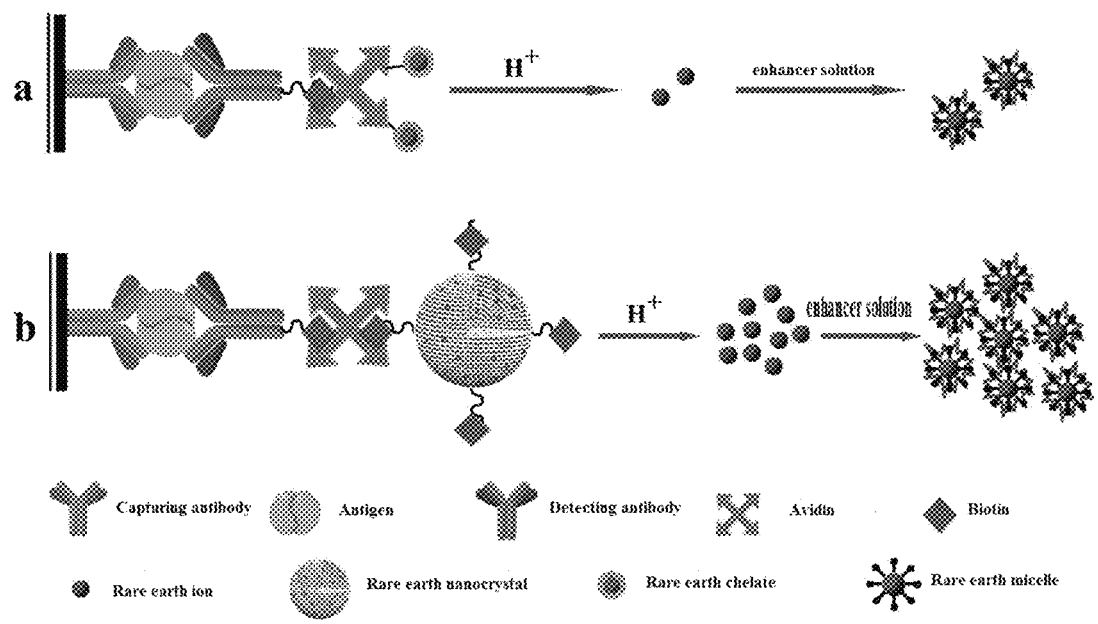
FIG. 1: Schematic diagram of (a) the conventional dissociation-enhanced lanthanide-based time-resolved fluorescence immunoassay (DELFIA) and (b) the dissolution-enhanced luminescent bioassay (DELBA) based on the rare earth nanomaterial of the present invention.

As shown in FIG. 1, each rare earth nanocrystal particle contains thousands of rare earth ions, and thus greatly improve the labeling ratio of rare earth ions, and upon addition of the enhancer solution a large number of molecules having strong fluorescence signals are formed, thereby significantly enhancing fluorescence signals and detection sensitivity.

Figure 2:
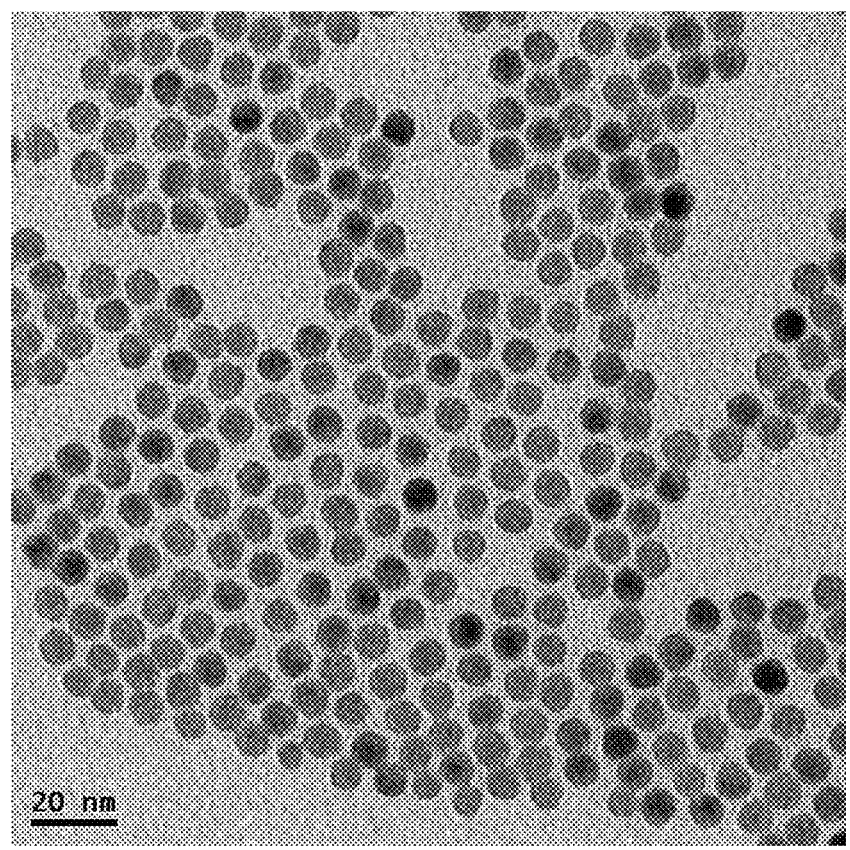

FIG. 2: Transmission electronmicroscopy (TEM) graph of NaEuF$_4$ nanocrystals. Instrument: Model JEM-2010; Manufacturer: JEOL.

Figure 3:
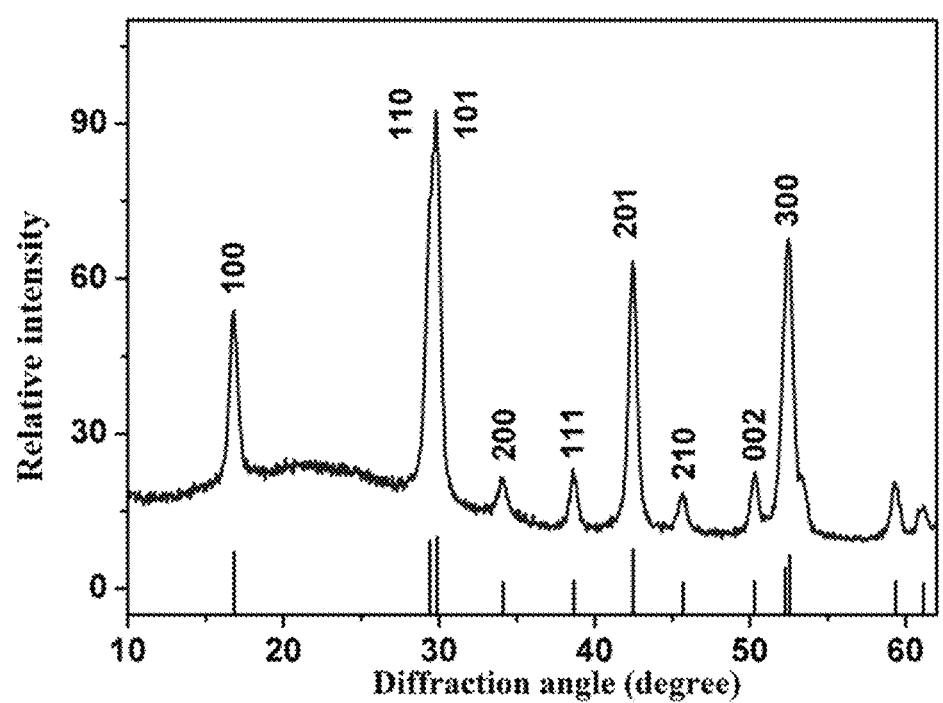

FIG. 3: Powder X-ray diffraction patterns of NaEuF$_4$ nanocrystals. Instrument: Model MiniFlex2; Manufacturer: Rigaku; Wave length of a copper target radiation: X=0.154187 nm.

Figure 4:
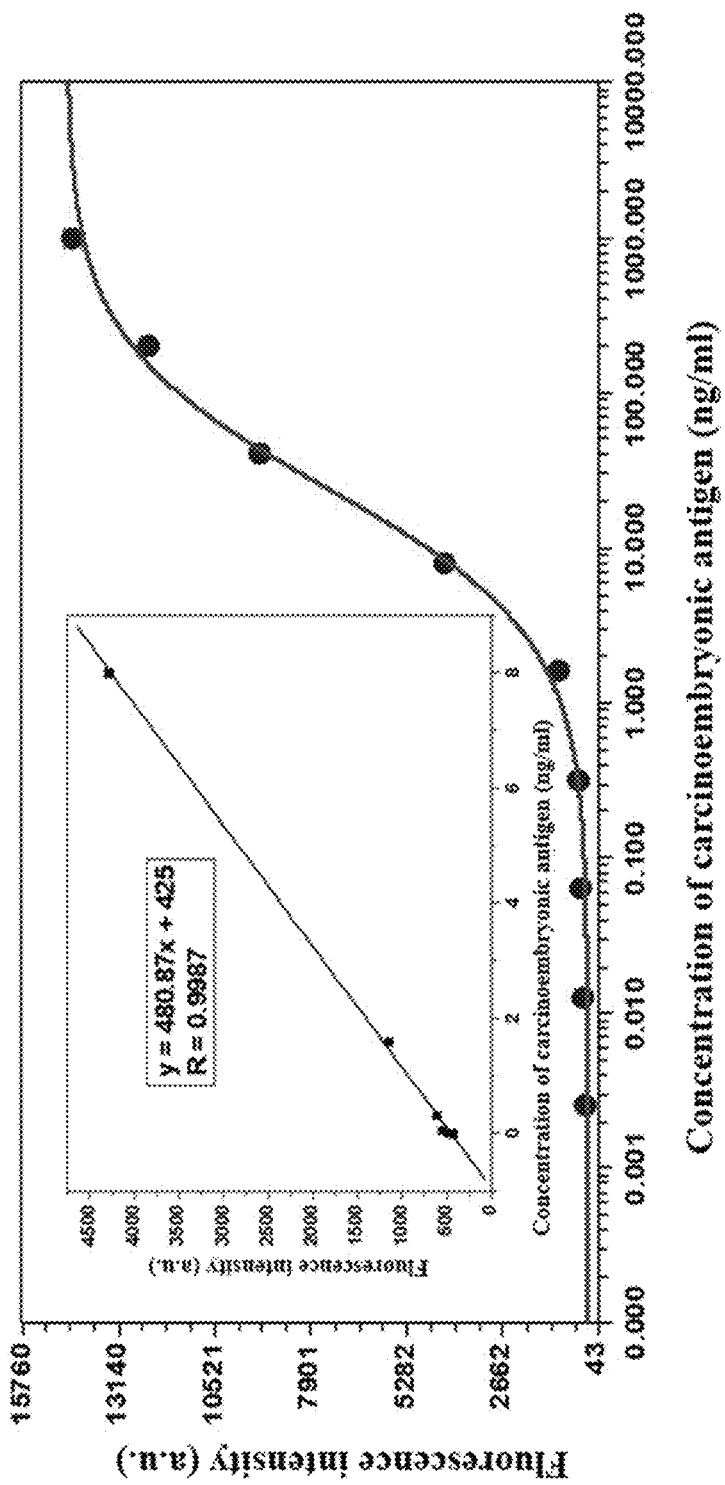

FIG. 4: Standard curve for the carcinoembryonic antigen assay using the double antibody sandwich method of the present invention.

Figure 5:
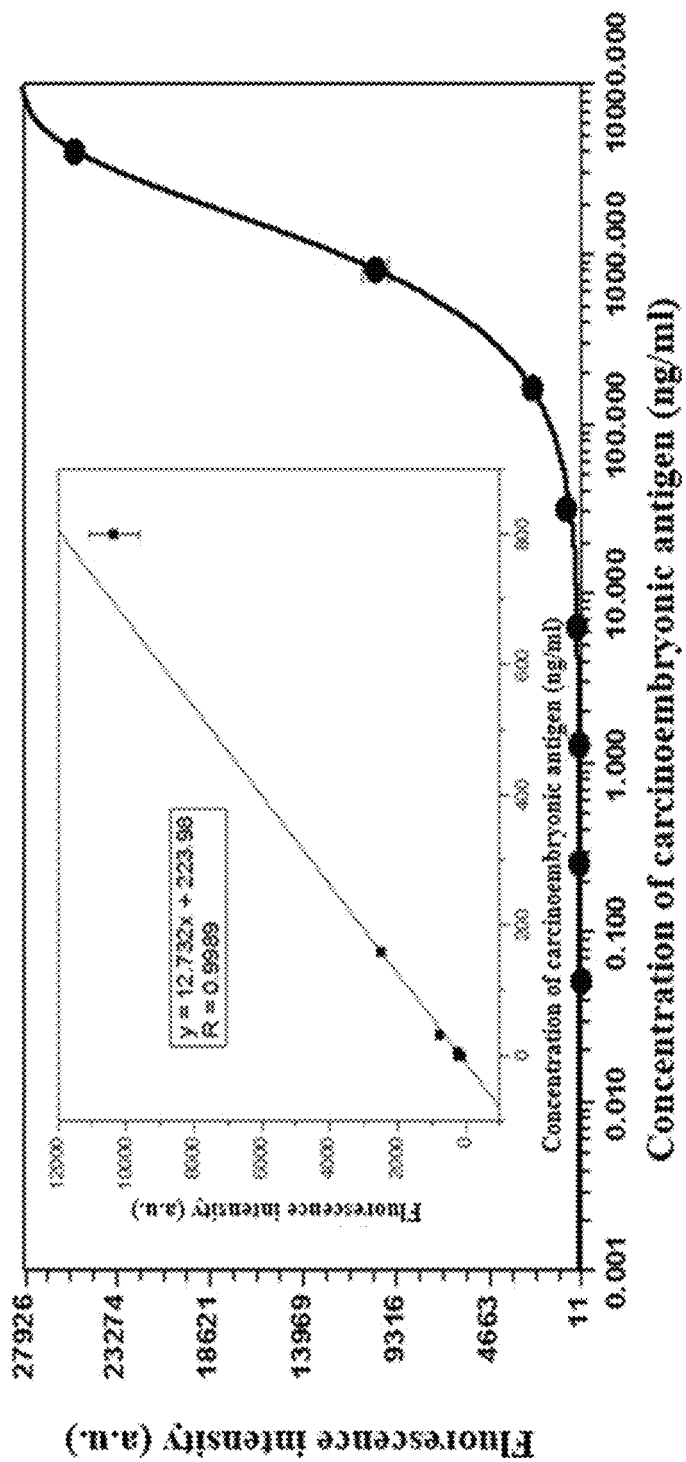

FIG. 5: Standard curve for the carcinoembryonic antigen assay using the commercial time-resolved carcinoembryonic antigen test kits.

SPECIFIC EMBODIMENTS

Hereinafter, the present invention will be illustrated with reference to the figures and the examples. However, the protection scope of the present invention should not be limited to the following examples. According to the disclosure of the present invention, those skilled in the art would recognize that the many changes and modifications based on the following examples belong to the protection scope of the present invention without departing from the technical features and the scope provided in the present invention.

EXAMPLES

Example 1

A process of dissolution-enhanced time-resolved fluoroimmunoassay based on the rare earth nanomaterial, comprising the following steps of:

1. Synthesis of NaEuF$_4$ Nanocrystals 1) weighing out 1 mmol of Eu(Ac)$_3$ and adding it into the mixed solvent of 6 mL of oleic acid and 15 ml of octadecene, excluding air and stirring at 160° C. under nitrogen atmosphere for 30 min to dissolve to give a solution A;

2) weighing out 150 mg of NH$_4$F and 100 mg of NaOH, adding them into methanol and dissolving to obtain a solution B;

3) after the solution A was cooled down to room temperature, slowly adding the solution B dropwise into the solution A with a dropper, excluding air, increasing temperature to 60° C. under nitrogen atmosphere, and stirring for 30 min to remove methanol;

4) increasing temperature to 120° C., and stirring the reaction for 10 min to remove residual water;

5) increasing temperature to 300° C. and stirring the reaction for 0.5 h;

6) after the solution cooled down to room temperature, adding two times the volume of anhydrous ethanol to precipitate the nanocrystals;

7) centrifuging, washing the nanocrystals with anhydrous ethanol for three times to be ready for use.

FIG. 2 and FIG. 3 respectively show the TEM image and Powder X-ray diffraction patterns of the synthesized NaEuF$_4$ nanocrystals.

2. Labeling Biotin or Antibody with NaEuF$_4$ Nanocrystals

A. labeling biotin with NaEuF$_4$ nanocrystals via chemical coordination method 1) weighing out 20 mg of the NaEuF$_4$ nanocrystals synthesized in step 1 to dissolve in 15 mL of hydrogen chloride-ethanol solution with a pH of 1.0, ultrasonicating for 30 min, collecting the nanoparticles by centrifugation, and then washing with anhydrous ethanol for three times to remove oleic acid on the surface of the nanocrystals, and adding 2 mL deionized water to dissolve to obtain 10 mg/mL water-soluble nanocrystals.

2) adding 1 mmol of biotin and two drops of ammonia water into the solution of step 1), ultrasonicating for 20 min, centrifuging washing with deionized water for three times, and finally dissolving in 1 mL of deionized water to be ready for use.

B. NaEuF$_4$ nanocrystals labeling antibody via physical adsorption method: taking 1 mL of the water-soluble nanocrystals synthesized in step A-1), adding 100 μg of antibody, adding 100 μl of the phosphate buffer solution with a pH of 8.0, shaking at room temperature for 1 h, collecting the nanoparticles by centrifugation, washing with water three for times, and dissolving in the buffer solution with a pH of 8.0 to be ready for use.

3. Preparation of an Enhancer Solution

Weighing out 1 g of Triton X-100, 26.6 mg of naphthoyl-trifluoroacetone, 193 mg of tri-n-octylphosphine oxide, adding distilled water to the volume of 1 L, and adjusting pH to 2.0 with diluted HCl to be ready for use.

4. Carcinoembryonic antigen detection using double-antibody sandwich assay based on NaEuF$_4$ nanocrystals 1) Coating: diluting the antibody against carcinoembryonic antigen to 10 μg/mL with 0.05 mol/L of carbonate buffer, which was then added to a 96-well polystyrene plate at 100 μL per well, incubating at 37° C. for 1 h, removing the liquid contained in each well, and washing three times with PBST washing buffer.

2) Blocking: formulating 2% of bovine serum albumin with 0.05 mol/L of carbonate buffer, which was then added to a 96-well plate at 300 μL per well, incubating at 37° C. for 1 h, removing the liquid contained in each well, and washing three times with PBST washing buffer.

3) Loading: formulating a series of standard solutions of carcinoembryonic antigen having concentrations in the range of 0.00256-1000 ng/mL with PBS buffer to provide standard samples respectively having the following concentrations: 0 ng/mL, 0.00256 ng/mL, 0.064 ng/mL, 0.0128 ng/mL, 0.32 ng/mL, 1.6 ng/mL, 8 ng/mL; incubating at 37° C. for 1 h, removing the liquid contained in each well, and washing three times with PBST washing buffer.

4) Adding NaEuF$_4$ nanocrystal labeled antibody: formulating 1 μg/mL of NaEuF$_4$ nanocrystal labeled antibody (prepared in the above step 2) with PBS buffer, which was then added to a 96-well plate at 100 μL per well, incubating at 37° C. for 1 h, removing the liquid contained in each well, and washing six times with PBST washing buffer.

5) Adding the enhancer solution: adding the enhancer solution at 200 μL per well, detecting fluorescence signals using time-resolved assays with the measurement parameters: excitation wavelength of 340 nm, emission wavelength of 615 nm, and delay time of 250 μs.

6) Plotting standard curve: plotting the standard curve with the concentration of the carcinoembryonic antigen standard solution as abscissa and the fluorescence intensity corresponding to each concentration of the standard solution as ordinate. As shown in FIG. 4, in the range of 0.00256-8 ng/mL, a linear correlation was observed between the concentration of the carcinoembryonic antigen and the fluorescence intensity, wherein y=480.87x+425, R=0.9987, and the limit of detection is 0.1 μg/mL, based on the blank mean plus three times the standard deviation (SD).

7) Testing sample: adding 100 μL of the test sample in step 3), while the other steps being the same as above, and calculating the corresponding concentration value by putting the fluorescence intensity of the sample into the standard curve equation.

8) Said step 4) can also be realized by the following steps:

(1) Adding the biotin-labeled antibody: formulating 1 μg/mL of biotin labeled antibody with PBS buffer, which was then added to a 96-well plate at 100 μL per well, incubating at 37° C. for 1 h, removing the liquid contained in each well, and washing three times with PBST washing buffer;

(2) Adding avidin: formulating 5 μg/mL of avidin with PBS buffer, which was then added to a 96-well plate at 100 μL per well, incubating at 37° C. for 0.5 h; removing the liquid contained in each well, and washing three times with PBST washing buffer;

(3) adding NaEuF$_4$ nanocrystal labeled biotin: formulating 10 μg/mL of NaEuF$_4$ nanocrystal labeled biotin (prepared in the above step 2) with PBS buffer, which was then added to a 96-well plate at 100 μL per well, incubating at 37° C. for 0.5 h, removing the solution contained in each well, and washing six times with PBST washing buffer.

Example 2: Comparison Between the Method According to the Invention and the Commercial Time-Resolved Carcinoembryonic Antigen Assay Kits 1) Coating: diluting the antibody against carcinoembryonic antigen to 10 μg/mL with 0.05 mol/L of carbonate buffer, which was then added to a 96-well polystyrene plate at 100 μL per well, incubating at 37° C. for 1 h, removing the liquid contained in each well, and washing three times with PBST washing buffer.

2) Blocking: formulating 2% of bovine serum albumin with 0.05 mol/L of carbonate buffer, which was then added to a 96-well plate at 300 μL per well, incubating at 37° C. for 1 h, removing the liquid contained in each well, and washing three times with PBST washing buffer.

3) Loading: formulating a series of standard solutions of carcinoembryonic antigen having concentrations in the range of 0.00256-1000 ng/mL with PBS buffer to provide standard samples respectively having the following concentrations: 0 ng/mL, 0.00256 ng/mL, 0.064 ng/mL, 0.0128 ng/mL, 0.32 ng/mL, 1.6 ng/mL, 8 ng/mL; incubating at 37° C. for 1 h, removing the liquid contained in each well, and washing three times with PBST washing buffer.

4) Adding the biotin-labeled antibody: formulating 1 μg/mL of biotin-labeled antibody with PBS buffer, which was then added to a 96-well plate at 100 μL per well, incubating at 37° C. for 1 h, removing the liquid contained in each well, and washing three times with PBST washing buffer.mL 5) Adding avidin: formulating 5 μg/mL of avidin with PBS buffer, which was then added to a 96-well plate at 100 μL per well, incubating at 37° C. for 0.5 h; removing the liquid contained in each well, and washing three times with PBST washing buffer.

6) Adding NaEuF$_4$ nanocrystal labeled biotin: formulating 10 μg/mL of NaEuF$_4$ nanocrystal labeled biotin (prepared in the above step 2 of Example 1) with PBS buffer, which was then added to a 96-well plate at 100 μL per well, incubating at 37° C. for 0.5 h, removing the solution in each well, and washing six times with PBST washing buffer.

7) Adding the enhancer solution: adding the enhancer solution at 200 μL per well, detecting fluorescence signals using time-resolved assays with the measurement parameters: excitation wavelength of 340 nm, emission wavelength of 615 nm, and delay time of 250 μs.

8) Plotting standard curve: plotting the standard curve with the concentration of the carcinoembryonic antigen standard solution as abscissa and the fluorescence intensity corresponding to each concentration of the standard solution as ordinate. As shown in FIG. 4, in the range of 0.00256-8 ng/mL, a linear correlation was observed between the concentration of the carcinoembryonic antigen and the fluorescence intensity, wherein y=480.87x+425, R=0.9987, and the limit of detection is 0.1 µg/mL, based on the blank mean plus three times the standard deviation (SD).

9) Detecting carcinoembryonic antigen by using time-resolved carcinoembryonic antigen assay kits: according to the operation of the description, plotting the standard curve. As shown in FIG. 5, in the range of 0.1-800 ng/mL, a linear correlation was observed between the concentration of the carcinoembryonic antigen and the fluorescence intensity, wherein y=12.732x+223.98, R=0.9989, and the limit of detection is 90 pg/mL, based on the blank mean plus three times the standard deviation (SD). The detection sensitivity of the present invention is 900 times higher than that of commercial time-resolved carcinoembryonic antigen assay kits.

Example 3

Comparison of the Recovery of Different Samples Determined by the Method According to the Present Invention and the Commercial Time-Resolved Carcinoembryonic Antigen Assay Kits 1) Coating: diluting the antibody against carcinoembryonic antigen to 10 µg/mL with 0.05 mol/L of carbonate buffer, which was then added to a 96-well polystyrene plate at 100 µL per well, incubating at 37° C. for 1 h, removing the liquid contained in each well, and washing three times with PBST washing buffer.

2) Blocking: formulating 2% of bovine serum albumin with 0.05 mol/L of carbonate buffer, which was then added to a 96-well plate at 300 µL per well, incubating at 37° C. for 1 h, removing the liquid contained in each well, and washing three times with PBST washing buffer.

3) Loading: formulating a series of standard solutions of carcinoembryonic antigen having concentrations in the range of 0.00256-1000 ng/mL with PBS buffer to provide standard samples respectively having the following concentrations: 0 ng/mL, 0.00256 ng/mL, 0.064 ng/mL, 0.0128 ng/mL, 0.32 ng/mL, 1.6 ng/mL, 8 ng/mL; incubating at 37° C. for 1 h, removing the liquid contained in each well, and washing three times with PBST washing buffer.

4) Adding $NaEuF_4$ nanocrystal labeled antibody: formulating 1 µg/mL of $NaEuF_4$ nanocrystal labeled antibody (prepared in the above step 2 of Example 1) with PBS buffer, which was then added to a 96-well plate at 100 µL per well, incubating at 37° C. for 1 h, removing the liquid contained in each well, and washing six times with PBST washing buffer.

5) Adding the enhancer solution: adding the enhancer solution at 200 µL per well, detecting fluorescence signals using time-resolved assays with the measurement parameters: excitation wavelength of 340 nm, emission wavelength of 615 nm, and delay time of 250 µs.

6) Plotting standard curve: plotting the standard curve with the concentration of the carcinoembryonic antigen standard solution as abscissa and the fluorescence intensity corresponding to each concentration of the standard solution as ordinate. In the range of 0.00256-8 ng/mL, a linear correlation was observed between the concentration of the carcinoembryonic antigen and the fluorescence intensity, wherein y=480.87x+425, R=0.9987.

7) Determining the recovery of serum and plasma matrices according to the present invention: dividing the same serum and the plasma containing EDTA anticoagulant into two portions respectively, one of which was added with 2 ng/mL of the carcinoembryonic antigen standard solution, adding 100 µL of the test samples in step 3), the other steps are the same as described above, testing each sample three times respectively, and calculating the corresponding concentration value of the test samples by putting the fluorescence intensity of the samples into the standard curve equation.

8) Determining the recovery of serum and plasma matrices by using the commercial time-resolved carcinoembryonic antigen assay kits: according to the operation of the description, plotting the standard curve. In the range of 0.1-800 ng/mL, a linear correlation was observed between the concentration of the carcinoembryonic antigen and the fluorescence intensity, wherein y=12.732x+223.98, R=0.9989, and determining the recovery of serum and plasma matrices as described in step 7).

9) Conclusion: as shown in Table 1, the recoveries of the serum matrices by the method of the present invention and by using the commercial time-resolved carcinoembryonic antigen assay kits were both above 95%, while regarding the plasma matrix containing EDTA anticoagulant, the recoveries were 95.2% and 85% respectively. Therefore it is indicated that the samples containing EDTA anticoagulant were negatively interfered by using the commercial time-resolved chelate labeled carcinoembryonic antigen assay kits, while they were not negatively interfered by the method of the present invention, therefore the method of the present invention has broader applicability.

TABLE 1

Comparison of the recovery of different samples determined by the method of the present invention and by using the commercial time-resolved carcinoembryonic antigen assay kits.

| Method | Sample | Background value (ng/mL) | Spiked value (ng/mL) | Theoretical value (ng/mL) | Measured value (ng/mL) | Average recovery (%) |
|---|---|---|---|---|---|---|
| Present invention | Serum | 5.8 | 2 | 7.8 | 7.6 ± 0.2 | 97.4 |
| | Plasma | 7.7 | 2 | 9.7 | 14.0 ± 0.3 | 95.2 |
| Commercial kits | Serum | 6.9 | 2 | 8.9 | 8.6 ± 0.2 | 96.2 |
| | Plasma | 8.9 | 2 | 10.9 | 9.3 ± 0.4 | 85.0 |

The invention claimed is:

1. A method of dissolution-enhanced time-resolved fluoroimmunoassay, comprising:
   obtaining an immune complex comprising a rare earth nanomaterial labeled biomolecule;
   dissolving the immune complex in an enhancer solution to release rare earth ions into the enhancer solution, wherein rare earth ions combine with chelates in the enhancer solution to form molecules capable of emitting fluorescence signals; and
   detecting the molecules using time-resolved fluoroimmunoassay, and
   wherein the rare earth nanomaterial is nanocrystal having a formula $XYF_4$, wherein X represents sodium, and Y represents europium.

2. The method according to claim 1, wherein the step of obtaining the immune complex comprises:
   1) immobilizing a capture antibody or antigen that specifically binds to a target antigen or a target antibody on a microplate through physical adsorption or covalent coupling;
   2) blocking the microplate with a blocking solution;
   3) adding a sample containing the target antigen or target antibody to the blocked microplate to allow binding of the target antigen or target antibody to the immobilized capture antibody or antigen; and 4) binding the rare earth nanomaterial labeled biomolecule to the bound target antigen or the target antibody to form the immune complex.

3. The method according to claim 2, wherein the sample contains the target antibody.

4. The method according to claim 2, wherein said binding of the rare earth nanomaterial labeled biomolecule of step 4) comprises:
   (a) adding a biotin-labeled antibody that specifically binds to the bound target antigen or antibody; and
   (b) adding the rare earth nanomaterial labeled with avidin to form the immune complex.

5. The method according to claim 1, wherein the enhancer solution comprises a buffer solution, β-diketone, a nonionic surfactant, and a synergistic agent.

6. The method according to claim 1, wherein the detection mode is sandwich assay, direct assay, or competitive assay.

7. The method according to claim 1, wherein the rare earth nanomaterial is labeled with the biomolecule via chemical coordination or physical adsorption to provide the rare earth nanomaterial labeled biomolecule.

8. The method according to claim 1, wherein the biomolecule is biotin, avidin, antibody, or aptamer.

* * * * *